United States Patent [19]

Okada et al.

[11] Patent Number: 4,861,777

[45] Date of Patent: Aug. 29, 1989

[54] PYRAZOLE DERIVATIVE AND INSECTICIDAL AND MITICIDAL COMPOSITION CONTAINING THE DERIVATIVE AS ACTIVE INGREDIENT

[75] Inventors: Itaru Okada, Kanagawa; Shuko Okui; Mana Nishimata, both of Tokyo; Yoji Takahashi, Machida; Toshiki Fukuchi, Yokohama, all of Japan

[73] Assignee: Mitsubishi Kasei Corporation, Tokyo, Japan

[21] Appl. No.: 241,387

[22] Filed: Sep. 7, 1988

[30] Foreign Application Priority Data

Sep. 11, 1987 [JP] Japan .................. 62-227735

[51] Int. Cl.$^4$ .................. C07D 231/56; C07D 413/08; C07D 403/08; A01N 43/90
[52] U.S. Cl. .................. 514/234.5; 514/232.5316; 514/322; 514/406; 544/80; 544/130; 544/140; 546/187; 546/199; 546/14; 548/369
[58] Field of Search .................. 548/80, 130, 140, 369; 546/187, 14, 199; 514/232.5, 234.5, 316, 322, 406

[56] References Cited

U.S. PATENT DOCUMENTS

| | | |
|---|---|---|
| 3,457,269 | 7/1969 | Kirchner . |
| 3,567,721 | 3/1971 | Wajngurt . |
| 3,875,182 | 4/1975 | Bretschneider et al. ............ 548/374 |
| 3,912,756 | 10/1975 | Wolff et al. .................. 548/492 |
| 3,937,822 | 2/1976 | DeLong et al. .................. 548/377 |
| 3,991,073 | 11/1976 | Mulder et al. .................. 548/369 |
| 4,005,100 | 1/1977 | Bretschneider et al. ............ 548/374 |
| 4,134,987 | 1/1979 | Huppatz .................. 548/377 |
| 4,214,090 | 7/1980 | Huppatz .................. 548/377 |
| 4,495,195 | 1/1985 | Beck et al. .................. 548/377 |
| 4,767,769 | 8/1988 | Hockley et al. .................. 514/234.5 |

FOREIGN PATENT DOCUMENTS

| | | |
|---|---|---|
| 6269 | 6/1972 | Japan . |
| 56671 | 3/1973 | Japan . |
| 73071 | 2/1981 | Japan . |
| 106665 | 11/1982 | Japan . |
| 34902 | 6/1985 | Japan . |
| 612674 | 8/1979 | Switzerland . |

OTHER PUBLICATIONS

*Farmaco, Ed. Sc.*, vol. 22, (1967), pp. 692–697, "Sintesi Di Derivati Pirazolici", by F. Rubessa.
*Rev. Roum. Chem.*, vol. 23, (1978), pp. 1581–1588, "Some Reactions of B-Aroyl-Acrylic Acid Epoxides", by M. A. El-Hashash and M. El-Kady.
*J. Phar. Sci.*, vol. 74, No. 9, Sep. 1985, pp. 1013–1015, "Synthesis and Anti-Inflammatory and Anagesic Activities of . . . ".
*Pest. Bio. Phy.*, vol. 25, (1986), pp. 163–168, "Pyrazole Carboxanilide Fungicides".

*Primary Examiner*—Mary C. Lee
*Assistant Examiner*—John A. H. Russell
*Attorney, Agent, or Firm*—Oblon, Spivak, McClelland, Maier & Neustadt

[57] ABSTRACT

A novel pyrazole derivative and an insecticidal or miticidal composition containing the derivative as the effective ingredient are disclosed.

The pyrazole derivative of the present invention has an excellent controlling effect also against harmful insects and mites exhibiting resistance to conventional insecticides and does not disturb the ecosystem since it is less toxic and less residual.

7 Claims, No Drawings

PYRAZOLE DERIVATIVE AND INSECTICIDAL AND MITICIDAL COMPOSITION CONTAINING THE DERIVATIVE AS ACTIVE INGREDIENT

BACKGROUND OF THE INVENTION

The present invention relates to a novel pyrazole derivative and an insecticidal and miticidal composition containing the derivative as an active ingredient.

Examples of compounds having similar structures to that of the compound of the present invention include the compounds described in Pest. Bio. Phy., 25, 163 (1986) and Japanese Patent Laid-Open (KOKAI) Nos. 52-87168 and 60-34949 which each have fungicidal activity; the compound described in Japanese Patent Laid-Open (KOKAI) No. 57-106665 which has herbicidal activity; and the compounds respectively described in Japanese Patent Laid-Open (KOKAI) Nos. 47-6269, 48-56671, 52-83840, 56-73071 and 59-95272, Japanese Patent Publication No. 55-44751 and J. Pharm. Sci., 74, 1013 (1985) which each have medicinal activity. However, there is no description with respect to insecticidal and miticidal activities. None of the above-described publications and literature also describes an aralkyl group as a substituent for the amino moiety of the compound.

On the other hand, Farmaco. Ed. Sci.,22, 692 (1967) describes N-benzyl-3-methyl-5-pyrazolecarboxamide and benzyl 3-methyl-5-pyrazolecarboxylate, Rev. Roum. Chim., 23, 1581 (1978) describes N-benzyl-1-(2,4-dinitrophenyl-3-biphenyl-5-pyrazolecarboxamide, and Japanese Patent Laid-Open (KOKAI) No. 50-58056 describes N-(4-hydroxybenzyl)-1,3-dimethyl-5-pyrazolecarboxamide and N-(4-hydroxycarbonylmethoxybenzyl)-1,3-dimethyl-5-pyrazolecarboxamide. However, none of these reports describes the presence of insecticidal and miticidal activities of the compounds given therein.

Although prior art is described above, there has been no report on a compound in which the acid moiety is a dicyclic pyrazole and the amide and (thio)alcohol ester moieties are aralkyl amide and aralkyl ester groups.

Since harmful insects have recently had resistance to insecticides due to use of insecticides for many years, it has been difficult to control insets by conventional insecticides. For example, insect having resistance to organophosphorous compounds and carbamate compounds which are both typical insecticides have been widely generated, resulting in the difficulty of control of these insects. In addition, the presence of insects having the resistance to synthetic pyrethloid-type insecticides which have recently attracted attention has been reported. On the other hand, some of the organophosphorous compounds or carbamate compounds exhibit high toxicity, and some of them disturb the ecological system due to their high residual effect to bring about an extremely anxious problem. Therefore, it is expected to develop a novel insecticide which exhibits an excellent controlling effect even against insects and mites having resistance to conventional insecticides and which has low toxicity and low residual effect.

As a result of the investigations performed by the present inventors for solving such a problem, a novel pyrazole derivative which has excellent insecticidal and miticidal acitvities has been found.

The present invention has been accomplished based on this finding.

SUMMARY OF THE INVENTION

In a first aspect of the present invention, there is provided a pyrazole derivative represented by the following formula (I):

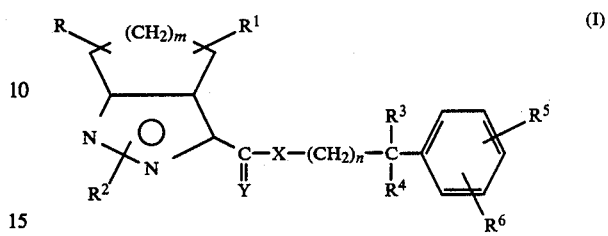

wherein R and $R^1$ independently represent a hydrogen atom or a $C_1$-$C_4$ alkyl group; $R^2$ represents a hydrogen atom, a $C_1$-$C_4$ alkyl group, a phenyl group or a benzyl group, which bonds to one of the nitrogen atoms of the pyrazole ring; $R^3$ and $R^4$ independently represent a hydrogen atom, a $C_1$-$C_4$ alkyl group or a phenyl group; $R^5$ and $R^6$ independently represent a hydrogen atom, a halogen atom, a $C_1$-$C_6$ alkyl group, a $C_3$-$C_6$ cycloalkyl group, a $C_1$-$C_4$ alkoxy group, a $C_1$-$C_4$ halogenoalkoxy group, a $C_1$-$C_4$ hydroxyalkoxy group, a $C_2$-$C_7$ alkoxyalkoxy group, a nitro group, a trifluoromethyl group, a phenyl group, a phenoxy group, a benzyloxy group, an amino group, a $C_1$-$C_4$ alkylamino group, a $C_2$-$C_8$ dialkylamino group, a cyano group, a carboxyl group, a $C_2$-$C_5$ alkoxycarbonyl group, a $C_4$-$C_7$ cycloalkoxycarbonyl group, a $C_3$-$C_9$ alkoxyalkoxycarbonyl group, a $C_2$-$C_7$ alkylaminocarbonyl group, a $C_3$-$C_{11}$ dialkylaminocarbonyl group, a piperidinocarbonyl group, a morpholinocarbonyl group, a trimethylsilyl group, a $C_1$-$C_4$ alkylthio group, a $C_1$-$C_4$ alkylsulfinyl group or a $C_1$-$C_4$ alkylsulfonyl group; X represents an oxygen atom a sulfur atom, NHO or $NR^7$ wherein $R^7$ represents a hydrogen atom or a $C_1$-$C_4$ alkyl group; Y represents an oxygen atom or a sulfur atom; m represents 1 or 2; and n represents 0 or 1.

In a second aspect of the present invention, there is provided an insecticidal and miticidal composition comprising, as the active ingredient, an insecticidally and miticidally effective amount of a pyrazole derivative represented by the following formula (I):

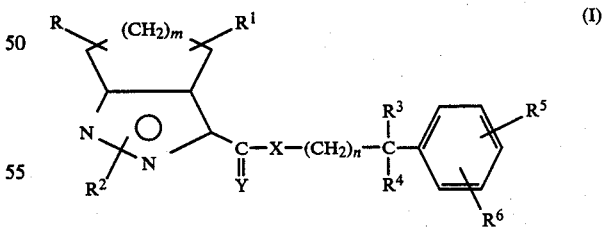

wherein R and $R^1$ independently represent a hydrogen atom or a $C_1$-$C_4$ alkyl group; $R^2$ represents a hydrogen atom, a $C_1$-$C_4$ alkyl group, a phenyl group or a benzyl group, which bonds to one of the nitrogen atoms of the pyrazole ring; $R^3$ and $R^4$ independently represent a hydrogen atom, a $C_1$-$C_4$ alkyl group or a phenyl group; $R^5$ and $R^6$ independently represent a hydrogen atom, a halogen atom, a $C_1$-$C_6$ alkyl group, a $C_3$-$C_6$ cycloalkyl group, a $C_1$-$C_4$ alkoxy group, a $C_1$-$C_4$ halogenoalkoxy group, a $C_1$-$C_4$ hydroxyalkoxy group, a $C_2$-$C_7$ alkoxyalkoxy group, a nitro group, a trifluoromethyl group, a phenyl group, a phenoxy group, a benzyloxy group, an amino group, a $C_1-C_4$ alkylamino group, a $C_2-C_8$ dialkylamino group, a cyano group, a carboxyl group, a $C_2-C_5$ alkoxycarbonyl group, a $C_4-C_7$ cycloalkoxycarbonyl group, a $C_3-C_9$ alkoxyalkoxycarbonyl group, a $C_2-C_7$ alkylaminocarbonyl group, a $C_3-C_{11}$ dialkylaminocarbonyl group, a piperidinocarbonyl group, a morpholinocarbonyl group, a trimethylsilyl group, a $C_1-C_4$ alkylthio group, a $C_1-C_4$ alkylsulfinyl group or a $C_1-C_4$ alkylsulfonyl group; X represents an oxygen atom, a sulfur atom, NHO or $NR^7$ wherein $R^7$ represents a hydrogen atom or a $C_1-C_4$ alkyl group; Y represents an oxygen atom or a sulfur atom; m represents 1 or 2; and n represents 0 or 1; and insecticidally and miticidally acceptable adjuvant(s).

In a third aspect of the present invention, there is provided a method for controlling insects and mites, which comprises applying an insecticidally and miticidally effective amount of a pyrazole derivative represented by the following formula (I):

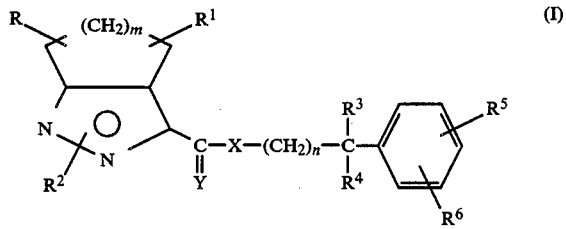
(I)

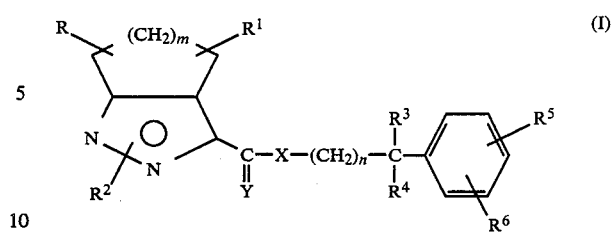
(I)

wherein R and $R^1$ independently represent a hydrogen atom or a $C_1-C_4$ alkyl group; $R^2$ represents a hydrogen atom, a $C_1-C_4$ alkyl group, a phenyl group or a benzyl group, which bonds to one of the nitrogen atoms of the pyrazole ring; $R^3$ and $R^4$ independently represent a hydrogen atom, a $C_1-C_4$ alkyl group or a phenyl group; $R^5$ and $R^6$ independently represent a hydrogen atom, a halogen atom, a $C_1-C_6$ alkyl group, a $C_3-C_6$ cycloalkyl group, a $C_1-C_4$ alkoxy group, a $C_1-C_4$ halogenoalkoxy group, a $C_1-C_4$ hydroxyalkoxy group, a $C_2-C_7$ alkoxyalkoxy group, a nitro group, a trifluoromethyl group, a phenyl group, a phenoxy group, a benzyloxy group, an amino group, a $C_1-C_4$ alkylamino group, a $C_2-C_8$ dialkylamino group, a cyano group, a carboxyl group, a $C_2-C_5$ alkoxycarbonyl group, a $C_4-C_7$ cycloalkoxycarbonyl group, a $C_3-C_9$ alkoxyalkoxycarbonyl group, a $C_2-C_7$ alkylaminocarbonyl group, a $C_3-C_{11}$ dialkylaminocarbonyl group, a piperidinocarbonyl group, a morpholinocarbonyl group, a trimethylsilyl group, a $C_1-C_4$ alkylthio group, a $C_1-C_4$ alkylsulfinyl group or a $C_1-C_4$ alkylsulfonyl group; X represents an oxygen atom, a sulfur atom, NHO or $NR^7$ wherein $R^7$ represents a hydrogen atom or a $C_1-C_4$ alkyl group; Y represents an oxygen atom or a sulfur atom; m represents 1 or 2; and n represents 0 or 1, which process comprises reacting a compound represented by the following formula (II):

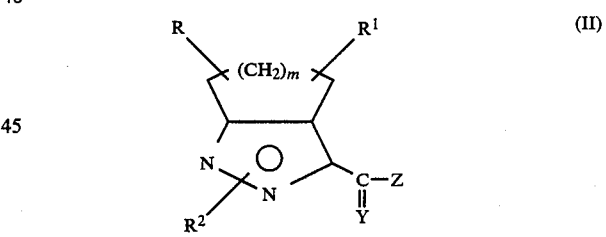
(II)

wherein R, $R^1$, $R^2$, Y and m are the same as those described above, and Z represents a chlorine atom, a bromine atom, a hydroxyl group, a methoxy group, an ethoxy group or a propoxy group, with a compound represented by the following formula (III):

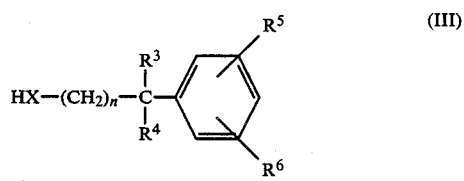
(III)

wherein R, $R^1$, $R^2$, Y and m are the same as those described above, and Z represents a chlorine atom, a bromine atom, a hydroxyl group, a methoxy group, an ethoxy group or a propoxy group, with a compound represented by the following formula (III):

wherein $R^3$, $R^4$, $R^5$, $R^6$ and n are the same as these described above, under the following conditions:
(i) when Z is a chlorine atom or a bromine atom, in the presence of a base in an aromatic hydrocarbon, ketone, halogenated hydrocarbon, water, ester or polar solvent at 0° to 30° C.; or (ii) when Z is a hydroxyl, methoxy, ethoxy or propoxy group, without using any solvent or in a high-boiling point solvent at 150° to 250° C.

DETAILED DESCRIPTION OF THE INVENTION

The present invention relates to a pyrazole derivative represented by the following formula (I) and an insecticidal or miticidal composition containing as an active ingredient the derivative:

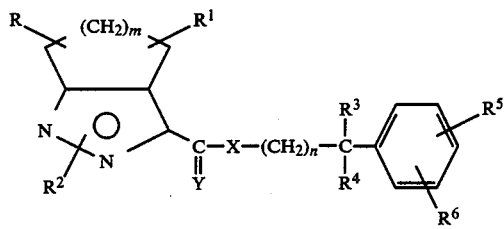

wherein R and $R^1$ independently represent a hydrogen atom or a $C_1$–$C_4$ alkyl group, $R^2$ represents a hydrogen atom, a $C_1$–$C_4$ alkyl group, a phenyl group or a benzyl group, which bonds to one of the nitrogen atoms of the pyrazole ring; $R^3$ and $R^4$ independently represent a hydrogen atom, a $C_1$–$C_4$ alkyl group or a phenyl group; $R^5$ and $R^6$ independently represent a hydrogen atom, a halogen atom, a $C_1$–$C_6$ alkyl group, a $C_3$–$C_6$ cycloalkyl group, a $C_1$–$C_4$ alkoxy group, a $C_1$–$C_4$ halogenoalkoxy group, a $C_1$–$C_4$ hydroxyalkoxy group, a $C_2$–$C_7$ alkoxyalkoxy group, a nitro group, a trifluoromethyl group, a phenyl group, a phenoxy group, a benzyloxy group, an amino group, a $C_1$–$C_4$ alkylamino group, a $C_2$–$C_8$ dialkylamino group, a cyano group, a carboxyl group, a $C_2$–$C_5$ alkoxycarbonyl group, a $C_4$–$C_7$ cycloalkoxycarbonyl group, a $C_3$–$C_9$ alkoxyalkoxycarbonyl group, a $C_2$–$C_7$ alkylamino carbonyl group, a $C_3$–$C_{11}$ dialkylaminocarbonyl group, a piperidinocarbonyl group, a morpholinocarbonyl group, a trimethylsilyl group, a $C_1$–$C_4$ alkylthio group, a $C_1$–$C_4$ alkyl-sulfinyl group or a $C_1$–$C_4$ alkylsulfonyl group; X represents an oxygen atom, a sulfur atom, NHO or $NR^7$ wherein $R^7$ represents a hydrogen atom or a $C_1$–$C_4$ alkyl group; Y represents an oxygen atom or a sulfur atom; m represents 1 or 2; and n represents 0 or 1.

The present invention is described in detail below.

In the formula (I):

R and $R^1$ independently represent a hydrogen atom or a $C_1$–$C_4$ straight chain or $C_3$–$C_4$ branched chain alkyl group such as a methyl, ethyl, n-propyl, isopropyl, n-butyl, isobutyl, secbutyl or t-butyl group;

$R^2$ represents a hydrogen atom, a $C_1$–$C_4$ straight chain or $C_3$–$C_4$ branched chain alkyl group such as a methyl, ethyl, n-propyl, isopropyl, n-butyl, isobutyl, sec-butyl or t-butyl group, a phenyl group or a benzyl group, which bonds to one of the nitrogen atoms of the pyrazole ring. Among these groups, a $C_1$–$C_4$ straight chain or $C_3$–$C_4$ branched chain alkyl group such as a methyl, ethyl, n-propyl, isopropyl, n-butyl, isobutyl, sec-butyl or t-butyl group is preferable and preferably bonds to the nitrogen at the 2-position of the pyrazole ring.

$R^3$ and $R^4$ independently represent a hydrogen atom, a $C_1$–$C_4$ straight chain or $C_3$–$C_4$ branched chain alkyl group such as a methyl, ethyl, n-propyl, isopropyl, n-butyl, isobutyl, sec-butyl or t-butyl group or a phenyl group, a hydrogen atom being preferable.

$R^5$ and $R^6$ independently represent a hydrogen atom, a halogen atom such as a fluorine, chlorine, bromine or iodine atom or a $C_1$–$C_6$ straight chain or $C_3$–$C_6$ branched chain alkyl group such as a methyl, ethyl, n-propyl, isopropyl, n-butyl, isobutyl, sec-butyl, t-butyl, n-amyl, isoamyl, t-pentyl, n-hexyl or 1-ethyl-1-methylpropyl group, a $C_3$–$C_6$ cycloalkyl group such as a cyclopropyl, cyclobutyl, cyclopentyl or cyclohexyl group, a $C_1$–$C_4$ straight chain or $C_3$–$C_4$ branched chain alkoxy group such as a methoxy, ethoxy, n-propoxy, isopropoxy, n-butoxy, isobutoxy, sec-butoxy or t-butoxy group, a $C_1$–$C_4$ halogenoalkoxy group such as a monofluoromethoxy, difluoromethoxy, trifluoromethoxy, 2,2,2-trifluoroethoxy, chloromethoxy, 2-chloroethoxy, 2-bromoethoxy, 3-chloropropoxy, 4-chlorobutoxy, 4-bromobutoxy or 1,1-dimethyl-2-chloroethoxy group, a $C_1$–$C_4$ hydroxyalkoxy group such as a hydroxymethoxy, 2-hydroxyethoxy, 3-hydroxypropoxy or 4-hydroxybutoxy group, a $C_2$–$C_7$ alkoxyalkoxy group such as a methoxymethoxy, ethoxymethoxy, methoxyethoxy, methoxypropoxy, methoxybutoxy, ethoxyethoxy, propoxyethoxy, butoxyethoxy or butoxypropoxy group, a nitro group, a trifluoromethyl group, a phenyl group, a phenoxy group, a benzyloxy group, an amino group, a $C_1$–$C_4$ straight chain or $C_3$–$C_4$ branched chain alkylamino group such as a methylamino, ethylamino, n-propylamino, isopropylamino, n-butylamino, isobutylamino, sec-butylamino or t-butylamino group, a $C_2$–$C_8$ di-(straight chain or branched chain alkyl)amino group such as a diemthylamino, diethylamino, di-n-propylamino, diisopropylamino, di-n-butylamino, diisobutylamino, N-ethylmethylamino, N-methylpropylamino, N-n-butylethylamino or N-isobutylamino group, a cyano group, a carboxyl group, a $C_2$–$C_5$ (straight chain or branched chain alkoxy)carbonyl group such as a methoxycarbonyl, ethoxycarbonyl, n-propoxycarbonyl, isopropoxycarbonyl, n-butoxycarbonyl, isobutoxycarbonyl, sec-butoxycarbonyl or t-butoxycarbonyl group, a $C_4$–$C_7$ cycloalkoxycarbonyl group such as a cyclopropoxycarbonyl, cyclobutoxycarbonyl, cyclopentyloxycarbonyl or cyclohexyloxycarbonyl, a $C_3$–$C_9$ alkoxyalkoxycarbonyl group such as a methoxymethoxycarbonyl, methoxyethoxycarbonyl, methoxypropoxycarbonyl, methoxybutoxycarbonyl, ethoxyethoxycarbonyl, n-propoxyethoxycarbonyl, isopropoxyethoxycarbonyl, n-, iso-, sec- or t-butoxyethoxycarbonyl or hexyloxyethoxycarbonyl group, a $C_2$–$C_7$ alkylaminocarbonyl group such as a methylaminocarbonyl, ethylaminocarbonyl, n-propylaminocarbonyl, isopropylaminocarbonyl, n-, iso-, sec- or t-butylaminocarbonyl, pentylaminocarbonyl or hexylaminocarbonyl group, a $C_3$–$C_{11}$ dialkylaminocarbonyl group such as a dimethylaminocarbonyl, diethylaminocarbonyl, dipropylaminocarbonyl, dibutylaminocarbonyl, dipentylaminocarbonyl, methylethylaminocarbonyl, methylpropylaminocarbonyl or ethylbutylaminocarbonyl group, a piperidinocarbonyl group, a morpholinocarbonyl group, a trimethylsilyl group, a $C_1$–$C_4$ straight chain or $C_3$–$C_4$ branched chain alkylthio group such as a methylthio, ethylthio, n-propylthio, isopropylthio, n-butylthio, isobutylthio, secbutylthio or t-butylthio group, a $C_1$–$C_4$ straight chain or $C_3$–$C_4$ branched chain alkylsulfinyl group such as a methylsulfinyl, ethylsulfinyl, n-propylsulfinyl, isopropylsulfinyl, n-butylsulfinyl, isobutylsulfinyl, sec-butylsulfinyl or t-butylsulfinyl group or a $C_1-C_4$ straight chain or $C_3-C_4$ branched chain alkylsulfonyl group such as a methylsulfonyl, ethylsulfonyl, n-propylsulfonyl, isopropylsulfonyl, n-butylsulfonyl, isobutylsulfonyl, sec-butylsulfonyl or t-butylsulfonyl group, and it is preferable that one of $R^5$ and $R^6$ is a hydrogen atom.

X represents an oxygen atom, a sulfur atom, NHO or $NR^7$, NH being preferable.

$R^7$ represents a hydrogen atom or a $C_1-C_4$ straight chain or $C_3-C_4$ branched chain alkyl group such as a methyl, ethyl, n-propyl, isopropyl, n-butyl, isobutyl, sec-butyl or t-butyl group, a hydrogen atom being preferable.

Y represents an oxygen atom or a sulfur atom, an oxygen being preferable.

Further, m represents 1 or 2, preferably 1 and n represents or 1, preferably 0.

The compound represented by the formula (I) can be produced in accordance with the following reaction scheme:

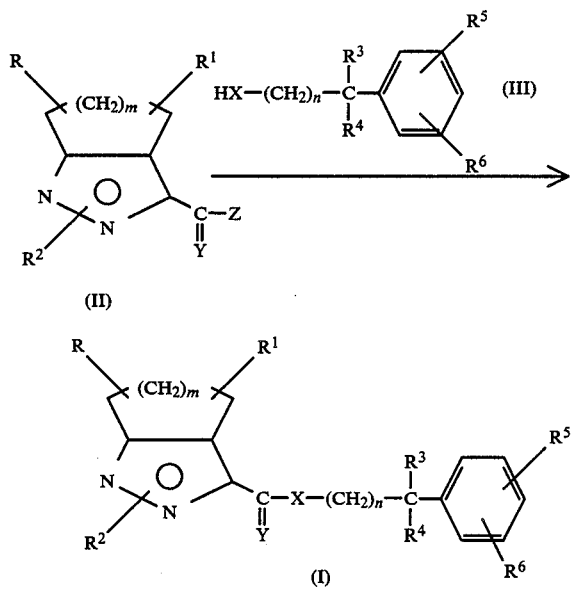

wherein R, $R^1$, $R^2$, $R^3$, $R^4$, $R^5$, $R^6$, X, Y, m and n each represents the same as that described for the formula (I); and Z represents a chlorine atom, a bromine atom, a hydroxyl group, a methoxy group, an ethoxy group or a propoxy group.

When Z in the above-described formula (II) is a chlorine atom or a bromine atom, the compound represented by the formula (I) can be obtained by reacting a compound represented by the formula (II) with a compound represented by the formula (III) at 0° to 30° C., preferably 0° to 5° C., in the presence of a base in an aromatic hydrocarbon such as benzene, toluene and xylene; a ketone such as acetone, methyl ethyl ketone and methyl isobutyl ketone; a halogenated hdrocarbon such as chloroform and methylene chloride; water; an ester such as methyl acetate and ethyl acetate; or a polar solvent such as tetrahydrofuran, acetonitrile, dioxane, N,N-dimethylformamide, N-methylpyrrolidone and dimethyl sulfoxide. Examples of bases include sodium hydroxide, potassium hydroxide, sodium carbonate, potassium carbonate, pyridine and triethylamine.

When Z in the above-described formula (II) is a hydroxyl group, a methoxy group, an ethoxy group or a propoxy group, the compound represented by the formula (I) can be obtained by reacting the compound represented by the formula (II) with the compound represented by the formula (III) at 150° to 250° C., preferably 200° to 250° C., without using any solvent or in a high-boiling point solvent such as N,N-dimethylformamide, N-methylpyrrolidone and dimethyl sulfoxide.

The compound represented by the formula (II) can be produced, for example, in accordance with the method described in Ann. Chem., 536, 97 (1938).

Although the compound represented by the formula (I) has a significant control activity against eggs and larvae of insects of Coleoptera, Lepidoptera, Hemiptera, Orthoptera, Diptera, as well as eggs and larvae of Spider mite. As a matter of course, insects and mites against which the compound represented by the formula (I) shows a remarkable controlling activity are not limited to those exemplified below.

1. Hemiptera; Planthoppers such as *Sogatella frucifera, Nilaparvata lugens, Laodelphax striatellus*, etc.; leafhoppers such as *Nephotettix cincticeps, Cicadella viridis*, etc. and Aphis such as *Myzus persicae*, etc.
2. Lepidoptera; *Spodoptera litura, Chilo suppressalis, Cnaphalocrosis medinalis*, etc.
3. Coleoptera; *Callosobruchus chinensis*, etc.
4 Diptera; *Musca domestica, Aedes aegypti, Culex pipiens molestus*, etc.
5 Spider mite; *Tetranychus urticae, Tetranychus cinnabarinus, Panonychus citri*, etc.

In the case of using the compound represented by the formula (I) according to the present invention as an insecticide or miticide, it may be used alone or usually formulated into emulsifiable concentrate, dust, wettable powder, solution, etc. together with adjuvants in the same manner as conventional agricultural chemicals and then used without or after dilution. The adjuvants are those used ordinarily for the formulation of the insecticides. For instance, there can be mentioned solid carrier such as talc, kaolin, diatomaceous earth, clay and starch; water; hydrocarbons such as cyclohexane, benzene, xylene and toluene; halogenated hydrocarbons such as chlorobenzene; ethers; amides such as dimethylformamide; ketones; alcohols; nitriles such as acetonitrile, as well as other known surface active agents such as emulsifiers and dispersing agents.

If desired, it is also possible to use in admixture or combination with other insecticides, miticides, fungicides, insect growth controlling agent, plant growth controlling agent, etc. Although the concentration for the effective ingredient in the formulated insecticidal or miticidal composition has no particular restrictions, it is usually contained from 0.5 to 20% by weight, preferably, from 1 to 10% by weight in dust; from 1 to 90% by weight, preferably, from 10 to 80% by weight in wettable powder; and from 1 to 90% by weight, preferably, from 10 to 40% by weight in emulsifiable concentrate.

In the case of using the compound represented by the formula (I) as the insecticide or miticide, it is usually used after dilution within the range of concentration of the active ingredient from 5 to 1000 ppm, preferably, from 10 to 500 ppm.

The present invention will be explained more specifically referring to the following preparation examples, formulation examples and test examples for the compound according to the present invention, but it should be understood that the present invention is not restricted only to the following examples.

EXAMPLE 1

Production of N-(4-t-butylbenzyl)-2-methyl-4,5,6,7-tetrahydro-3-(2H)-indazolecarboxamide A mixture of 1.80 g of 2-methyl-4,5,6,7-tetrahydro-3-(2H)-indazolecarboxylic acid and 11.7 g of thionyl chloride was refluxed under heating for 1 hour. Thionyl chloride was distilled off under reduced pressure, and the residue was dissolved in 20 ml of toluene. The thus-obtained solution was dropwisely added to 25 ml of a toluene solution containing 1.96 g of 4-t-butylbenzylamine and 1.21 g of triethylamine at 0° to 5° C. After the completion of addition, the thus-obtained mixture was agitated for 2 hours and then poured into ice water, followed by extraction with toluene. The toluene layer was washed with an aqueous sodium carbonate, water and a saturated saline solution. After drying the extract over anhydrous sodium sulfate, it was concentrated under reduced pressure. The residue was purified by silica gel column chromatography to obtain 2.88 g of Compound No. 18 shown in Table 1.

The NMR and IR spectra of this compound were as follows: $^1$HNMR (CDCl$_3$)δppm; 1.3 (s, 9H), 1.7 (m, 4H), 2.6 (m, 4H), 4.05 (s, 3H), 4.5 (d, 2H), 5.8 (b, 1H), 7.3 (m, 4H) IR (KBr) cm$^{-1}$; 3362, 2932, 1636, 1540, 1445, 1293, 970, 590.

EXAMPLE 2

Production of N-(4-t-butylbenzyl)-2-methylcyclopenta-[1,2-C]-3-pyrazolecarboxamide A mixture of 1.94 g of ethyl 2-methylcyclopenta[1,2-C]-3-pyrazolecarboxylate and 2.45 g of 4-t-butylbenzylamine was agitated under heating at 200° C. for 4 hours. After the thus-obtained mixture had been cooled to room temperature, the mixture was purified by silica gel column chromatography to obtain 2.15 g of Compound No. 6 shown in Table 1.

The NMR and IR spectra of this compound were as follows: $^1$HNMR (CCl$_4$)δppm; 1.35 (s, 9H), 2.3-2.8 (m, 6H), 4.1 (s, 3H), 4.5 (d, 2H), 5.8 (b, 1H), 7.25 (m, 4H) IR (KBr) cm$^{-1}$; 3310, 2960, 1640, 1560, 1540, 1370, 1320, 580.

EXAMPLE 3

Production of N-(4-n-butylbenzyl)-2,4,6-trimethylcyclopenta[1,2-C]-3-pyrazolecarboxamide A mixture of 1.94 g of 2,4,6-trimethylcyclopenta[1,2-C]-3-pyrazolecarboxylic acid and 11.7 g of thionyl chloride was refluxed under heating for 1 hour. After thionyl chloride was distilled off under reduced pressure, the residue was dissolved in 20 ml of ethyl acetate. The thus-obtained solution was dropwisely added to 25 ml of a ethyl acetate solution containing 1.96 g of 4-n-butylbenzylamine and 1.21 g of triethylamine at 0° to 5° C. After the completion of addition, the thus-obtained mixture was agitated for 2 hours and poured into ice water, followed by extraction with ethyl acetate. The ethyl acetate layer was washed with an aqueous solution of sodium carbonate, water and a saturated saline solution. The extract was then dried over anhydrous sodium sulfate and then concentrated under reduced pressure. The residue was purified by silica gel column chromatography to obtain Compound No. 68 shown in Table 1 and then Compound No. 69 shown in Table 1. Compound Nos. 68 and 69 were diastereomers.

The NMR, IR and MASS spectra of these compounds were as follows:

Spectra of Compound No. 68

$^1$HNMR (CDCl$_3$)δppm; 0.9 (m, 3H), 1.05 (d, 3H), 1.25 (d, 3H), 1.0-1.8 (m, 4H), 2.15 (m, 2H), 2.55 (t, 2H), 3.1 (m, 2H), 4.1 (s, 3H), 4.5 (d, 2H), 5.95 (b, 1H), 7.25 (m, 4H).

IR (KBr) cm$^{-1}$; 3280, 2950, 2860, 1635, 1550, 1530, 450, 1370, 1275, 980, 810, 530 MASS; 339 (M+), 177

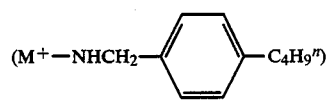

Spectra of Compound No. 69

$^1$HNMR (CDCl$_3$)δppm; 0.9 (m, 3H), 1.2 (d, 3H), 1.3 (d, 3H), 1.0-1.8 (m, 4H), 2.6-3.3 (m, 6), 4.15 (s, 3H), 4.55 (d, 2H), 6.0 (b, 1H), 7.25 (m, 4H).

IR (KBr) cm$^{-1}$; 3290, 2950, 1640, 1550, 1520, 1300, 980, 800, 520. MASS; 339 (M+), 177

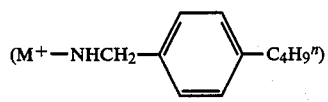

EXAMPLE 4

The compounds shown in Tables 1 and 2 were obtained in accordance with the method of Example 1, 2 or 3.

TABLE 1
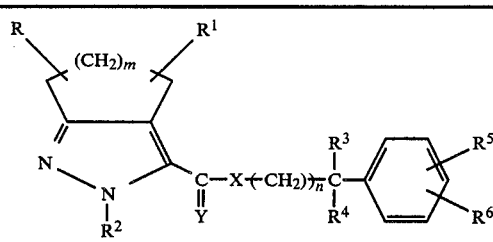
| Compound No. | R, R¹, (CH₂)ₘ | R² | X | Y | -(CH₂)ₙ-C(R³)(R⁴)-Ar(R⁵,R⁶) | Refractive Index (n_D) Melting Point (°C.) |
|---|---|---|---|---|---|---|
| 1 | 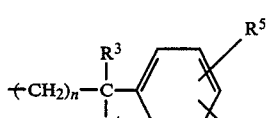 | —CH₃ | —NH— | O | —CH₂—C₆H₅ | 149–151 |
| 2 | " | " | " | " | —CH₂—C₆H₄—$C_3H_7^i$ | 98–100 |
| 3 | " | " | " | " | —CH₂—C₆H₄—$C_4H_9^n$ | 98–101 |
| 4 | " | " | " | " | —CH₂—C₆H₄—$C_4H_9^i$ | 92–93 |
| 5 |  | —CH₃ | —NH— | O | —CH₂—C₆H₄—$C_4H_9^{sec}$ | $n_D^{24.5}$ 1.5632 |
| 6 | " | " | " | " | —CH₂—C₆H₄—$C_4H_9^t$ | 94–95 |
| 7 | " | " | " | " | —CH₂—C₆H₄—CF₃ | 163–165 |
| 8 | " | " | " | " | —CH₂—C₆H₄—cyclopropyl | 102–110[1] |
| 9 | " | " | " | " | —CH₂—C₆H₄—O—$C_3H_7^i$ | 99–101 |
| 10 | 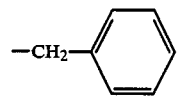 | —CH₃ | —NH— | O | —CH₂—C₆H₃(CH₃)(CH₃) | 143–145 |

TABLE 1-continued

| Compound No. | R (CH₂)ₘ R¹ structure | R² | X | 4 | -(CH₂)ₙ-C(R³)(R⁴)-Ar(R⁵,R⁶) structure | Refractive Index (n_D) Melting Point (°C.) |
|---|---|---|---|---|---|---|
| 11 | " | —CH₃ | —O— | " | —CH₂—C₆H₄—O—C₆H₅ (3-phenoxybenzyl) | 64–65 |
| 12 | " | —C₂H₅ | —NH— | " | —CH₂—C₆H₄—C₄H₉ᵗ (4-tert-butylbenzyl) | 115–117 |
| 13 | " | —C₃H₇ⁱ | " | " | " | 130–132 |
| 14 | " | —C₄H₉ⁿ | " | " | —CH₂—C₆H₄—C₄H₉ᵗ | 122–123 |
| 15 | cyclopentyl | phenyl | —NH— | O | —CH₂—C₆H₄—C₄H₉ᵗ | 193–195 |
| 16 | methyl-cyclopentyl | —CH₃ | " | " | " | n_D^{24.5} 1.5465 |
| 17 | cyclohexyl | " | " | " | —CH₂—C₆H₄—C₃H₇ⁱ | 128–130 |
| 18 | " | " | " | " | —CH₂—C₆H₄—C₄H₉ᵗ | 117–118 |
| 19 | " | " | " | " | —CH(CH₃)—C₆H₄—C₄H₉ᵗ | 144–145 |
| 20 | cyclohexyl | —CH₃ | —NH— | O | —CH₂—C₆H₄—CF₃ | 144–145 |

TABLE 1-continued

General structure:

$$\text{pyrazoline ring with substituents R, R}^1\text{, (CH}_2)_m\text{, N-R}^2\text{, C(=Y)-X-(CH}_2)_n\text{-CR}^3\text{R}^4\text{-C}_6\text{H}_3(\text{R}^5)(\text{R}^6)$$

| Compound No. | R, R¹, (CH₂)ₘ group | R² | X | Y | (CH₂)ₙ–CR³R⁴–aryl(R⁵,R⁶) group | Refractive Index (n_D) / Melting Point (°C.) |
|---|---|---|---|---|---|---|
| 21 | " | " | " | " | –CH₂–C₆H₄–Cl (4-Cl) | 159–160 |
| 22 | " | " | " | " | –CH₂–C₆H₄–Cl (2-Cl) | 122–125 |
| 23 | " | –CH₂–C₆H₅ | " | " | –CH₂–C₆H₄–C₄H₉ᵗ | 116–119 |
| 24 | methylcyclohexyl | –CH₃ | " | " | " | 164–166 |
| 25 | cyclopentyl | –CH₃ | –NH– | O | –CH₂–CH₂–C₆H₄–C₄H₉ᵗ | 106–108 |
| 26 | " | " | " | " | –CH₂–C₆H₄–C(CH₃)₂–CH₂CH₃ | 80–82 |
| 27 | " | " | " | " | –CH₂–C₆H₄–CH₃ | 163–164 |
| 28 | " | " | " | " | –CH₂–C₆H₄–C₃H₇ⁿ | 114–118² |
| 29 | " | " | " | " | –CH₂–C₆H₄–C₆H₁₁ (cyclohexyl) | 114–119³ |
| 30 | cyclopentyl | –CH₃ | –NH– | O | –CH(CH₃)–C₆H₄–C₆H₅ | 134–135 |

TABLE 1-continued

| Compound No. | R, (CH₂)ₘ, R¹ | R² | X | 4 | (CH₂)ₙ, R³, R⁴, R⁵, R⁶ | Refractive Index (n_D) Melting Point (°C.) |
|---|---|---|---|---|---|---|
| 31 | " | " | " | " | —CH₂—⟨C₆H₄⟩—OCH₃ | 125–126 |
| 32 | " | " | " | " | —CH₂—⟨C₆H₄⟩—OC₃H₇ⁿ | 118–119 |
| 33 | " | " | " | " | —CH₂—⟨C₆H₄⟩—O—⟨C₆H₅⟩ (meta) | 135–137 |
| 34 | " | " | " | " | —CH₂—⟨C₆H₄⟩—O—⟨C₆H₅⟩ (para) | 111–112 |
| 35 | cyclopentyl | —CH₃ | —NH— | O | —CH₂—⟨C₆H₄⟩—OCH₂CH₂OC₃H₇ⁿ | 101–102 |
| 36 | " | " | " | " | —CH₂—⟨C₆H₄⟩—OCH₂CH₂OH | 146–147 |
| 37 | " | " | " | " | —CH₂—⟨C₆H₄⟩—F | 142–144 |
| 38 | " | " | " | " | —CH₂—⟨C₆H₄⟩ (2-CF₃) | 150–151 |
| 39 | " | " | " | " | —CH₂—⟨C₆H₄⟩ (3-CF₃) | 131–132 |

TABLE 1-continued

| Compound No. | R, R¹, (CH₂)ₘ group | R² | X | Y | -(CH₂)ₙ-CR³R⁴-aryl group | Refractive Index (n_D) Melting Point (°C.) |
|---|---|---|---|---|---|---|
| 40 | cyclopentane (1,2-disubstituted) | —CH₃ | —NH— | O | —CH₂—C₆H₄—OCHF₂ | 127–128 |
| 41 | " | " | " | " | —CH₂—C₆H₄—OCH₂CF₃ | 146–147 |
| 42 | " | " | " | " | —CH₂—C₆H₄—COOC₂H₅ | 111–112 |
| 43 | " | " | " | " | —CH₂—C₆H₄—COOC₃H₇$^i$ | 121–123 |
| 44 | " | " | " | " | —CH₂—C₆H₄—COOC₄H₉$^t$ | 94–96 |
| 45 | cyclopentane | —CH₃ | —NH— | O | —CH₂—C₆H₄—COO—C₆H₁₁ | 91–93 |
| 46 | " | " | " | " | —CH₂—C₆H₄—CONHC₃H₇$^n$ | 177–179 |
| 47 | " | " | " | " | —CH₂—C₆H₄—NO₂ | 174–176 |
| 48 | " | " | " | " | —CH₂—C₆H₄—NH₂ | 166–167 |
| 49 | " | " | " | " | —CH₂—C₆H₄—NHC₃H₇$^n$ | 103–104 |

TABLE 1-continued

Structure:
$$\begin{array}{c} R\diagdown(CH_2)_m\diagup R^1 \\ \text{pyrazole ring with } N-N-R^2, C=Y \\ -C(=Y)-X-(CH_2)_n-C(R^3)(R^4)-\text{Ar}(R^5,R^6) \end{array}$$

| Compound No. | R−(CH₂)ₘ−R¹ | R² | X | Y | −(CH₂)ₙ−CR³R⁴−Ar(R⁵,R⁶) | Refractive Index (n_D) Melting Point (°C.) |
|---|---|---|---|---|---|---|
| 50 | cyclopentyl | —CH₃ | —NH— | O | —CH₂—C₆H₄—N(CH₃)₂ (para) | 163–164 |
| 51 | " | " | " | " | —CH₂—C₆H₄—N(C₃H₇ⁿ)₂ (para) | 106–107 |
| 52 | " | " | " | " | —CH₂—C₆H₄—CN (para) | 179–181 |
| 53 | " | " | " | " | —CH₂—C₆H₄—SCH₃ (para) | 129–130 |
| 54 | " | " | " | " | —CH₂—C₆H₄—S(O)CH₃ (para) | 129–131 |
| 55 | cyclopentyl | —CH₃ | —NH— | O | —CH₂—C₆H₄—S(O)₂CH₃ (para) | 152–153 |
| 56 | " | " | " | " | —CH₂—C₆H₃(OCH₃)(C₄H₉ᵗ) | 177–179 |
| 57 | " | " | " | " | —CH₂—C₆H₃Cl₂ | 173–174 |
| 58 | " | " | " | " | —C(CH₃)₂—C₆H₅ | 103–104 |
| 59 | " | " | —O— | " | —CH₂—C₆H₄—C₄H₉ᵗ (para) | 61–63 |

TABLE 1-continued

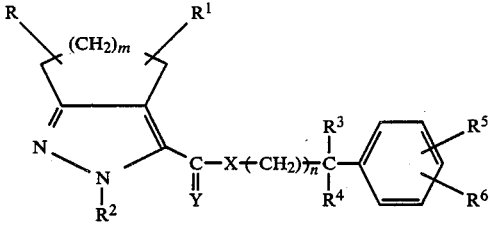

| Compound No. | R―(CH₂)ₘ― structure | $R^2$ | X | 4 | ―(CH₂)ₙ―C(R³)(R⁴)―Ar(R⁵)(R⁶) | Refractive Index ($n_D$) Melting Point (°C.) |
|---|---|---|---|---|---|---|
| 60 | 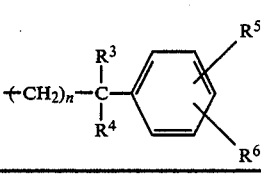 | ―CH₃ | ―S― | O | ―CH₂―C₆H₄―C₄H₉ᵗ | 74–75 |
| 61 | " | " | ―N(CH₃)― | " | ―CH₂―C₆H₅ | $n_D^{25}$ 1.5678 |
| 62 | 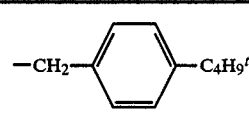 | " | ―NH― | " | ―CH₂―C₆H₄―C₃H₇ⁱ | 121–122 |
| 63 | " | " | " | " | ―CH₂―C₆H₄―C₄H₉ⁿ | 114–116 |
| 64 | " | " | " | " | ―CH₂―C₆H₄―C₅H₁₁ⁿ | 101–102 |
| 65 | 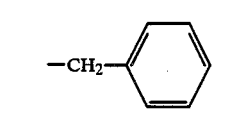 | ―CH₃ | ―NH― | O | ―CH₂―C₆H₄―C(CH₃)₂―CH₂―CH₃ | 84–86 |
| 66 | 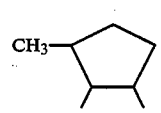 | " | " | " | ―CH₂―C₆H₄―C₄H₉ᵗ | 103–104⁴ |
| 67 | " | " | " | " | " | 111–112⁴ |
| 68 | " | " | " | " | ―CH₂―C₆H₄―C₄H₉ⁿ | 79–81⁵ |
| 69 | " | " | " | " | ―CH₂―C₆H₄―C₄H₉ⁿ | 127–129⁵ |
| 70 | 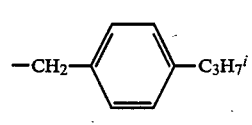 | ―CH₃ | ―NH― | O | ―CH₂―C₆H₄―CF₃ | 136–137⁶ |

TABLE 1-continued

| Compound No. | R, R¹, (CH₂)ₘ group | R² | X | 4 | -(CH₂)ₙ-C(R³)(R⁴)- aryl group | Refractive Index (nD) Melting Point (°C.) |
|---|---|---|---|---|---|---|
| 71 | " | " | " | " | " | 195–197[6] |
| 72 | cyclopentyl | " | " | " | -CH₂-C₆H₄-COOC₂H₄OC₂H₅ | 128–130 |
| 73 | " | " | " | " | -CH₂-C₆H₄-C₆H₅ | 146–148 |
| 74 | " | -C₄H₉ᵗ | " | " | -CH₂-C₆H₄-C₄H₉ᵗ | 131–132 |
| 75 | cyclopentyl | -CH₃ | -NH- | O | -CH₂-(o-CH₃-C₆H₄) | 135–136 |
| 76 | " | " | " | " | -CH(C₆H₅)₂ | 157–158 |
| 77 | methylcyclopentyl | " | " | " | -CH₂-C₆H₄-O-C₆H₅ | 109–110 |
| 78 | cyclopentyl | " | " | " | -CH₂-C₆H₄-OCH₂-C₆H₅ | 110–111 |
| 79 | " | " | " | " | -CH₂-C₆H₄-CON(CH₃)₂ | 146–147 |
| 80 | cyclopentyl | -CH₃ | -NH- | O | -CH₂-C₆H₄-CON(morpholino) | 146–148 |

TABLE 1-continued

Structure:
$$\text{Pyrazoline-based compound with R, R}^1\text{, (CH}_2)_m\text{, R}^2\text{, X, Y, (CH}_2)_n\text{, R}^3\text{, R}^4\text{, R}^5\text{, R}^6$$

| Compound No. | R, R¹, (CH₂)ₘ group | R² | X | Y | (CH₂)ₙ, R³, R⁴, aryl, R⁵, R⁶ group | Refractive Index (n_D) Melting Point (°C.) |
|---|---|---|---|---|---|---|
| 81 | " | " | " | " | —CH₂—C₆H₄—CON(piperidinyl) | 149–151 |
| 82 | " | " | " | " | —CH(CH₃)—C₆H₄—Br (meta) | 127–128 |
| 83 | " | " | " | S | —CH₂—C₆H₄—C₄H₉ᵗ | 109–110 |
| 84 | " | " | —N(CH₃)— | O | —CH₂—C₆H₄—C₄H₉ᵗ | n_D²⁵ 1.5452 |
| 85 | cyclopentyl | —CH₃ | —NHO— | O | —CH₂—C₆H₄—COOC₄H₉ᵗ | 125–126 |
| 86 | cyclopentyl (C₂H₅ substituted) | " | —NH— | " | —CH₂—C₆H₄—C₄H₉ᵗ | 120–122 |
| 87 | " | " | " | " | —CH₂—C₆H₄—C₄H₉ⁿ | 112–114 |
| 88 | cyclopentyl | —H | " | " | —CH₂—C₆H₄—C₄H₉ᵗ | 178–180 |
| 89 | " | —CH₃ | " | " | —CH₂—C₆H₄—Si(CH₃)₃ | n_D²⁵ 1.5545 |
| 90 | cyclopentyl | —CH₃ | —NH— | O | —CH(CH(CH₃)₂)—C₆H₄—OCH₃ (meta) | 80–81 |

TABLE 1-continued

Structure:

R—(CH₂)ₘ—R¹ backbone with pyrazole ring system: C(=Y)—X—(CH₂)ₙ—C(R³)(R⁴)—phenyl(R⁵,R⁶); N—N—R²

| Compound No. | R—(CH₂)ₘ—R¹ | R² | X | 4 | —(CH₂)ₙ—C(R³)(R⁴)—phenyl(R⁵,R⁶) | Refractive Index ($n_D$) Melting Point (°C.) |
|---|---|---|---|---|---|---|
| 91 | " | " | " | " | —CH(CH₃)(CH₃)—C₆H₄—OCH₂—C₆H₅ | 102–103 |
| 92 | " | " | " | " | —CH₂CH₂—C₆H₄—OCH₃ | 106–108 |

Note:

[1] This compound exhibited a broad range of melting points because it contained about 50% of

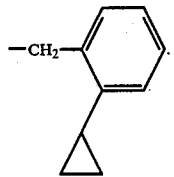

[2] This compound exhibited a broad range of melting points because it contained about 20% of

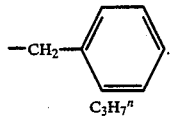

[3] This compound exhibited a broad range of melting points because it contained about 20% of

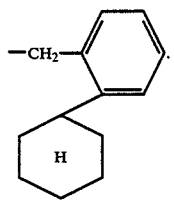

[4] Compound Nos. 66 and 67 were diastereomers and Compound No. 66 exhibited a higher $R_f$ value than that of Compound No. 67 in TLC (thin layer chromatography).
[5] Compound Nos. 68 and 69 were diastereomers and Compound No. 68 exhibited a higher $R_f$ value than that of Compound No. 69 in TLC.
[6] Compound Nos. 70 and 71 were diastereomers and Compound No. 70 exhibited a higher $R_f$ value than that of Compound No. 71 in TLC.

TABLE 2

$$\begin{array}{c} R \diagdown \quad (CH_2)_m \quad \diagup R^1 \\ \diagdown \diagup \\ \underset{R^2}{N}-N \diagdown C-X-(CH_2)_n-\underset{R^4}{\overset{R^3}{C}}-\diagup \diagdown \underset{R^6}{\overset{R^5}{\diagdown}} \\ \overset{\|}{Y} \end{array}$$

| Compound No. | $\diagdown \underset{\diagup \diagdown}{(CH_2)_m} \diagup^{R^1}$ | $R^2$ | X | Y | $-(CH_2)_n-\underset{R^4}{\overset{R^3}{C}}-\underset{R^6}{\diagup \diagdown}\overset{R^5}{\diagdown}$ | Refractive Index ($n_D$) Melting Point (°C.) |
|---|---|---|---|---|---|---|
| 93 | (cyclopentyl) | $CH_3$ | NH | O | $-CH_2-$⟨phenyl⟩$-C_4H_9{}^t$ | 109–111 |
| 94 | (cyclohexyl) | $-CH_2-$⟨phenyl⟩ | " | O | " | 101–103 |
| 95 | $CH_3-$(cyclopentyl)$-CH_3$ | $CH_3$ | " | " | $-CH_2-$⟨phenyl⟩$-CF_3$ | 60–65[7] |

Note:
[7] This compound exhibited a broad range of melting points because it contained all isomers.

Formulation Examples of the compound of the present invention are shown below. The terms "parts" and "%" represent "parts by weight" and "% by weight", respectively.

FORMULATION EXAMPLE 1: WETTABLE POWDER

A wettable powder containing 40% of an active ingredient was prepared by uniformly mixing and pulverizing 20 parts of each of the compounds of the present invention shown in Tables 1 and 2, 20 parts of Carplex #80 (trade name, produced by Shionogi Seiyaku Co.), 55 parts of N,N Kaolin Clay (trade name, produced by Tsuchiya Kaolin Co.) and 5 parts of higher alcohol sulfuric acid ester type surfactant Sorpol 8070 (trade name, Toho Kagaku Co.).

FORMULATION EXAMPLE 2: DUST

A dust containing 2% of an active ingredient was prepared by uniformly mixing and pulverizing 2 parts of each of the compounds of the present invention shown in Tables 1 and 2, 93 parts of clay (produced by Nippon Talc Co.) and 5 parts of white carbon.

FORMULATION EXAMPLE 3: EMULSIFIABLE CONCENTRATE

In a mixed solvent containing 35 parts of xylene and 30 parts of dimethylformamide, was dissolved 20 parts of each of the compounds of the present invention shown in Tables 1 and 2. Then, 15 parts of polyoxyethylene type surfactant Sorpol 3005X (trade name, produced by Toho Kagaku Co.) was added to the obtained solution to obtain an emulsifiable concentrate containing 20% of an active ingredient.

FORMULATION EXAMPLE 4: FLOWABLE AGENT

A stable flowable agent containing 30% of the effective ingredients was prepared by mixing and dispersing 30 parts of the compound according to the present invention shown in Tables 1 to 3 and a previously prepared mixture of 8 parts of ethylene glycol, 5 parts of Sorpol AC 3032 (trademark, manufactured by Toho Kagaku Co.) and 0.1 part of xanthene gum into 56.9 parts of water, and then pulverizing the slurrylike mixture in the wet process in a DYNO-MILL (manufactured by Shinmaru Enterprises Co.).

TEST EXAMPLE 1: EFFECT AGAINST ADULST
*Tetranychus urticae*

Then female adult *Tetranychus urticae* were put to a leaf disc (2 cm diameter) of a kidney bean leaf. Then, 5 ml of a solution, prepared by diluting each of insecticidal and miticidal compositions of the present invention formulated in accordance with the preparation of Formulation Example 1 with water to a predetermined concentration, was scattered by using a rotary type scattering tower (manufactured by Mizuho Rika Co.). Test was repeated twice for each concentration.

Twenty four hours after the treatment, the number of live and dead larvae were counted and the miticidal activity (%) was determined by the following equation.

$$\text{Miticidal Activity (\%)} = \frac{\text{Number of dead larvae}}{\text{Number of treated larvae}} \times 100$$

The results are shown in Table 3.

TEST EXAMPLE 2: EFFECT AGAINST EGGS OF *Tetranychus urticae*

Five female adult *Tetranychus urticae* were put to a leaf disc (2 cm diameter) of a kidney bean leaf. The mites were allowed to oviposit on the leaf disc for 20 hours after putting and then the adult females mites were removed. Then, 5 ml of a solution prepared by diluting each of insecticidal and miticidal compositions of the present invention formulated in accordance with the preparation of Formulation Example 1 with water to a predetermined concentration was scattered by using a rotary type scattering tower (manufactured by Mizuho Rika Co.). Test was repeated twice for each concentration.

The number of unhatched eggs and the number of hatched larvae were counted 5 days after the treatment to determine the ovicidal activity (%) by the following equation.

$$\text{Ovicidal Activity (\%)} = \frac{\text{Number of unhatched eggs}}{\text{Number of unhatched eggs} + \text{Number of hatched eggs}}$$

The results are shown in Table 3.

TABLE 3

| Compound No. | Concentration (ppm) | Miticidal activity (%) | Ovicidal activity (%) |
|---|---|---|---|
| 2 | 500 | 100 | 100 |
| 3 | " | " | " |
| 4 | " | " | " |
| 5 | " | " | " |
| 6 | " | " | " |
| 8 | " | " | " |
| 9 | " | " | " |
| 13 | " | " | " |
| 16 | " | " | " |
| 17 | " | " | " |
| 18 | " | " | " |
| 20 | " | " | " |
| 23 | " | " | " |
| 26 | " | " | " |
| 29 | " | " | " |
| 44 | " | " | " |
| 51 | " | " | " |
| 62 | " | " | " |
| 63 | " | " | " |
| 64 | " | " | " |
| 65 | " | " | " |
| 66 | " | " | " |
| 67 | " | " | " |
| 86 | " | " | " |
| 87 | " | " | " |
| 89 | " | " | " |

TEST EXAMPLE 3: EFFECT AGAINST LARVAE OF *Nilaparvata lugens*

Germinated seedlings of rice plant were set to a glass cylinder (3 cm diameter, 17 cm length) and five larvae of fourth instar of *Nilaparvata lugens* were put to them. Then, each of the insecticidal and miticidal compositions according to the present invention formulated in accordance with the preparation of Formulation Example 3 was diluted with water and scattered by 0.5 ml using a scattering tower (manufactured by Mizuho Rika Co.). Test was repeated four times for each concentration. Twenty-four hours after the treatment, the number of dead larvae was counted to determine the mortality (%). The results are shown in Table 4.

TEST EXAMPLE 4: EFFECT AGAINST LARVAE OF *Plutella xylostella*

Slices of cabbage leaves (5 x 5 cm) were immersed for one minute in a water-diluted solution of each of the insecticidal and miticidal compositions of the present invention formulated in accordance with the preparation of Formulation Example 1. They were air dried after immersion and placed in a plastic cup (7 cm diameter), to which five larvae of third instar of *Plutella xylostella* were put. Test was repeated twice for each concentration.

Four days after putting, the number of dead larvae was counted to determine the mortality (%).

The results are shown in Table 5.

TABLE 4

| Compound No. | Concentration (ppm) | Mortality (%) |
|---|---|---|
| 3 | 500 | 100 |
| 4 | " | " |
| 5 | " | " |
| 6 | " | " |
| 10 | " | " |
| 16 | " | " |
| 17 | " | " |
| 22 | " | " |
| 25 | " | " |
| 28 | " | " |
| 29 | " | " |
| 31 | " | " |
| 32 | " | " |
| 34 | " | " |
| 35 | " | " |
| 42 | " | " |
| 43 | " | " |
| 44 | " | " |
| 49 | " | " |
| 51 | " | " |
| 62 | " | " |
| 63 | " | " |
| 64 | " | " |
| 65 | " | " |
| 69 | " | " |
| 77 | " | " |
| 79 | " | " |
| 86 | " | " |
| 87 | " | " |
| 89 | " | " |

TABLE 5

| Compound No. | Concentration (ppm) | Mortality (%) |
|---|---|---|
| 2 | 500 | 100 |
| 3 | " | " |
| 5 | " | " |
| 6 | " | " |
| 7 | " | " |
| 8 | " | " |
| 9 | " | " |
| 15 | " | " |
| 16 | " | " |
| 17 | " | " |
| 24 | " | " |
| 28 | " | " |
| 32 | " | " |
| 34 | " | " |
| 35 | " | " |
| 41 | " | " |
| 44 | " | " |
| 49 | " | " |
| 51 | " | " |
| 62 | " | " |

TABLE 5-continued

| Compound No. | Concentration (ppm) | Mortality (%) |
|---|---|---|
| 63 | " | " |
| 64 | " | " |
| 65 | " | " |
| 67 | " | " |
| 69 | " | " |
| 77 | " | " |
| 79 | " | " |
| 86 | " | " |
| 87 | " | " |
| 89 | " | " |

What is claimed is:

1. A pyrazole derivative represented by the following formula (I):

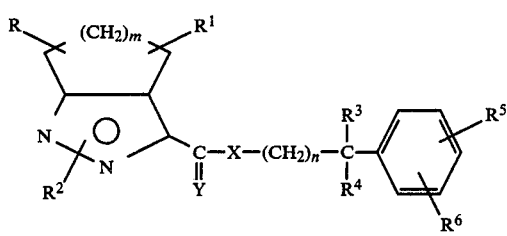

wherein R and $R^1$ independently represent a hydrogen atom or a $C_1$-$C_4$ alkyl group; $R^2$ represents a hydrogen atom, a $C_1$-$C_4$ alkyl group, a phenyl group or a benzyl group, which bonds to one of the nitrogen atoms of the pyrazole ring; $R^3$ and $R^4$ independently represent a hydrogen atom, a $C_1$-$C_4$ alkyl group or a phenyl group; $R^5$ and $R^6$ independently represent a hydrogen atom, a halogen atom a $C_1$-$C_6$ alkyl group, a $C_3$-$C_6$ cycloalkyl group, a $C_1$-$C_4$ alkoxy group, a $C_1$-$C_4$ halogenoalkoxy group, a $C_1$-$C_4$ hydroxyalkoxy group, a $C_2$-$C_7$ alkoxyalkoxy group, a nitro group, a trifluoromethyl group, a phenyl group, a phenoxy group, a benzyloxy group, an amino group, a $C_1$-$C_4$ alkylamino group, a $C_2$-$C_8$ dialkylamino group, a cyano group, a carboxyl group, a $C_2$-$C_5$ alkoxycarbonyl group, a $C_4$-$C_7$ cycloalkoxycarbonyl group, a $C_3$-$C_9$ alkoxyalkoxycarbonyl group, a $C_2$-$C_7$ alkylaminocarbonyl group, a $C_3$-$C_{11}$ dialkylaminocarbonyl group, a piperidinocarbonyl group, a morpholinocarbonyl group, a trimethylsilyl group, a $C_1$-$C_4$ alkylthio group, a $C_1$-$C_4$ alkylsulfinyl group or a $C_1$-$C_4$ alkylsulfonyl group; X represents an oxygen atom, a sulfur atom, NHO or $NR^7$ wherein $R^7$ represents a hydrogen atom or a $C_1$-$C_4$ alkyl group; Y represents an oxygen atom or a sulfur atom; m represents 1 or 2; and n represents 0 or 1.

2. The pyrazole derivative according to claim 1, wherein $R^2$ is a $C_1$-$C_4$ alkyl group, Y is an oxygen atom, X is $NR^7$, and $R^3$, $R^4$, $R^5$ and $R^7$ are each a hydrogen atom, and n is 0.

3. The pyrazoe derivative according to claim 2, wherein $R^2$ bonds to the nitrogen atom at the 2-position of said pyrazole ring and m is 1.

4. An insecticidal and miticidal composition comprising, as the active ingredient, an insecticidally and miticidally effective amount of a pyrazole derivative represented by the following formula (I):

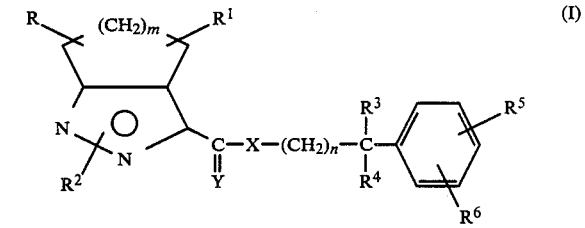

wherein R and $R^1$ independently represent a hydrogen atom or a $C_1$-$C_4$ alkyl group; $R^2$ represents a hydrogen atom, a $C_1$-$C_4$ alkyl group, a phenyl group or a benzyl group, which bonds to one of the nitrogen atoms of the pyrazole ring; $R^3$ and $R^4$ independently represent a hydrogen atom, a $C_1$-$C_4$ alkyl group or a phenyl group; $R^5$ and $R^6$ independently represent a hydrogen atom, a halogen atom, a $C_1$-$C_6$ alkyl group, a $C_3$-$C_6$ cycloalkyl group, a $C_1$-$C_4$ alkoxy group, a $C_1$-$C_4$ halogenoalkoxy group, a $C_1$-$C_4$ hydroxyalkoxy group, a $C_2$-$C_7$ alkoxyalkoxy group, a nitro group, a trifluoromethyl group, a phenyl group, a phenoxy group, a benzyloxy group, an amino group, a $C_1$-$C_4$ alkylamino group, a $C_2$-$C_8$ dialkylamino group, a cyano group, a carboxyl group, a $C_2$-$C_5$ alkoxycarbonyl group, a $C_4$-$C_7$ cycloalkoxycarbonyl group, a $C_3$-$C_9$ alkoxyalkoxycarbonyl group, a $C_2$-$C_7$ alkylamino carbonyl group, a $C_3$-$C_{11}$ dialkylaminocarbonyl group, a piperidinocarbonyl group, a morpholinocarbonyl group, a trimethylsilyl group, a $C_1$-$C_4$ alkylthio group, a $C_1$-$C_4$ alkylsulfinyl group or a $C_1$-$C_4$ alkylsulfonyl group;

X represents an oxygen atom, a sulfur atom, NHO or $NR^7$ wherein $R^7$ represents a hydrogen atom or a $C_1$-$C_4$ alkyl group; Y represents an oxygen atom or a sulfur atom; m represents 1 or 2; and n represents 0 or 1; and insecticidally and miticidally acceptable adjuvant(s).

5. The insecticidal and miticidal composition according to claim 4, wherein $R^2$ is a C alkyl group, Y is an oxygen atom, X is $NR^7$, and $R^3$, $R^4$, $R^5$ and $R^7$ are each a hydrogen atom, and n is 0.

6. The insecticidal and miticidal composition according to claim 5, wherein $R^2$ bonds to the nitrogen atom at the 2-position of said pyrazole ring and m is 1.

7. A method for controlling insects and mites, which comprises applying an insecticidally and miticidally effective amount of a pyrazole derivative represented by the following formula (I):

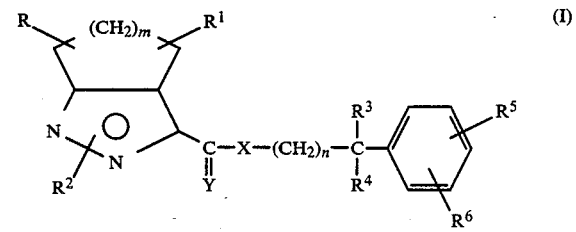

wherein R and $R^1$ independently represent a hydrogen atom or a $C_1$-$C_4$ alkyl group; $R^2$ represents a hydrogen atom, a $C_1$-$C_4$ alkyl group, phenyl group or a benzyl group, which bonds to one of the nitrogen atoms of the pyrazole ring; $R^3$ and $R^4$ independently represent a hydrogen atom, a $C_1$-$C_4$ alkyl group or a phenyl group; $R^5$ and $R^6$ independently represent a hydrogen atom, a halogen atom, a $C_1$–$C_6$ alkyl group, a $C_3$–$C_6$ cycloalkyl group, a $C_1$–$C_4$ alkoxy group, a $C_1$–$C_4$ halogenoalkoxy group, a $C_1$–$C_4$ hydroxyalkoxy group, a $C_2$–$C_7$ alkoxyalkoxy group, a nitro group, a trifluoromethyl group, a phenyl group, a phenoxy group, a benzyloxy group, an amino group, a $C_1$–$C_4$ alkylamino group, a $C_2$–$C_8$ dialkylamino group, a cyano group, a carboxyl group, a $C_2$–$C_5$ alkoxycarbonyl group, a $C_4$–$C_7$ cycloalkoxycarbonyl group, a $C_3$–$C_9$ alkoxyalkoxycarbonyl group, a $C_2$–$C_7$ alkylaminocarbonyl group, a $C_3$–$C_{11}$ dialkylaminocarbonyl group, a piperidinocarbonyl group, a morpholinocarbonyl group, a trimethylsilyl group, a $C_1$–$C_4$ alkylthio group, a $C_1$–$C_4$ alkylsulfinyl group or a $C_1$–$C_4$ alkylsulfonyl group;

X represents an oxygen atom, a sulfur atom, NHO or $NR^7$ wherein $R^7$ represents a hydrogen atom or a $C_1$–$C_4$ alkyl group; Y represents an oxygen atom or a sulfur atom; m represents 1 or 2; and n represents 0 or 1, to eggs or larvae of said insects or mites.

* * * * *